United States Patent
Dogo-Isonagie et al.

(10) Patent No.: US 10,744,075 B2
(45) Date of Patent: Aug. 18, 2020

(54) ORAL CARE PRODUCTS AND WHITENING COMPOSITIONS THEREOF

(71) Applicant: Colgate-Palmolive Company, New York, NY (US)

(72) Inventors: Cajetan Dogo-Isonagie, Highland Park, NJ (US); Paloma Pimenta, Staten Island, NY (US); Chun Huang, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 87 days.

(21) Appl. No.: 16/011,739

(22) Filed: Jun. 19, 2018

(65) Prior Publication Data

US 2018/0360708 A1 Dec. 20, 2018

Related U.S. Application Data

(60) Provisional application No. 62/521,815, filed on Jun. 19, 2017.

(51) Int. Cl.
*A61K 8/22* (2006.01)
*A61K 8/23* (2006.01)
*A61Q 11/00* (2006.01)

(52) U.S. Cl.
CPC .............. *A61K 8/22* (2013.01); *A61K 8/23* (2013.01); *A61Q 11/00* (2013.01); *A61K 2800/31* (2013.01); *A61K 2800/882* (2013.01)

(58) Field of Classification Search
CPC . A61K 9/46; A61K 7/16; A61K 31/74; A61K 6/00

USPC .......................................................... 433/204
See application file for complete search history.

(56) References Cited

U.S. PATENT DOCUMENTS

| 5,031,178 A | 7/1991 | Cornell |
| 6,083,488 A * | 7/2000 | Riccobono ............... A61K 8/02 424/44 |
| 2009/0175917 A1 | 7/2009 | Engelbrecht et al. |
| 2017/0172864 A1 | 6/2017 | Evans |

FOREIGN PATENT DOCUMENTS

| AT | 397766 | 6/1994 |
| GB | 1453432 | 10/1976 |
| GB | 1483501 | 8/1977 |
| GB | 2290234 | 12/1995 |
| WO | 199721420 | 6/1997 |
| WO | 2000/009079 | 2/2000 |
| WO | 200016737 | 3/2000 |
| WO | 2007147815 | 12/2007 |

OTHER PUBLICATIONS

Toh, C. G., "Clinical evaluation of a dual-activated bleaching system", Asian Journal of Aesthetic Dentistry, vol. 1, No. 2, p. 65-70 (1993).

* cited by examiner

*Primary Examiner* — Walter E Webb

(57) ABSTRACT

An oral care product, a whitening composition thereof, and methods for the same are disclosed therein. The oral care product includes an orally acceptable vehicle and the whitening composition. The whitening composition includes a whitening booster and a source of hydrogen peroxide. The whitening booster may include a salt of a monopersulfate.

16 Claims, No Drawings

ORAL CARE PRODUCTS AND WHITENING COMPOSITIONS THEREOF

CROSS-REFERENCE TO RELATED APPLICATIONS

This application claims priority to U.S. Provisional Patent Application No. 62/521,815, filed Jun. 19, 2017, which is incorporated by reference herein.

BACKGROUND

Conventional oral care products (e.g., mouthwashes, toothpastes, gels, etc.) including whitening agents are often utilized to whiten teeth. For example, conventional mouthwashes including hydrogen peroxide are often utilized to oxidize chromophores bound to surfaces and/or dentin of teeth to thereby whiten the teeth. While mouthwashes including hydrogen peroxide have proven to be effective for whitening teeth, different chromophores on the surfaces are often oxidized at varying rates and/or via varying mechanisms. Accordingly, mouthwashes including a single whitening agent (e.g., hydrogen peroxide) may require relatively longer periods of treatment to appreciably whiten the teeth.

In view of the foregoing, oral care products incorporating hydrogen peroxide often include an additional whitening agent to facilitate the oxidation of the different chromophores to thereby shorten the periods of treatment. While the oral care products incorporating a variety of whitening agents have demonstrated increased efficacy in whitening teeth, there is a desire to utilize whitening agents having relatively increased reactivity to thereby further reduce the periods of treatment. However, the whitening agents having relatively increased reactivity are often unstable and/or subject to degradation. For example, the whitening agents having relatively increased reactivity often react with other components of the dentifrice (e.g., water) and/or degrade, thereby reducing the effectiveness thereof.

What is needed, then, are improved whitening compositions and methods for whitening teeth.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a whitening composition including a whitening booster and a source of hydrogen peroxide, wherein the whitening booster comprises a salt of a monopersulfate.

In at least one implementation, the salt of the monopersulfate is an alkali metal salt of the monopersulfate.

In another implementation, the whitening booster includes potassium monopersulfate.

In another implementation, the whitening booster includes only the salt of the monopersulfate.

In another implementation, the whitening composition consists of or consists essentially of the whitening booster and the source of hydrogen peroxide. As used herein, consists essentially of the whitening booster and the source of hydrogen peroxide may refer to include the whitening booster and the source of hydrogen peroxide, as well as any substance, compound, material, or the like that does not materially affect the combination of the whitening booster and the source of hydrogen peroxide, and/or that does not interact synergistically with the whitening booster and/or the source of hydrogen peroxide to increase the whitening efficacy of the whitening composition. As such, consists essentially of the whitening booster and the source of hydrogen peroxide means that the composition may include any additional substance, compound, material, or the like that does not materially interact and/or interact synergistically with the whitening booster and/or the source of hydrogen peroxide to increase the whitening efficacy of the whitening composition.

In another implementation, the whitening composition further includes an orally acceptable vehicle, and the whitening booster is maintained separate from the orally acceptable vehicle and the source of hydrogen peroxide until the point of use.

In another implementation, the whitening composition is substantially free of water.

In another implementation, the whitening composition further includes a buffering agent.

In another implementation, the buffering agent includes at least one of sodium bicarbonate and sodium carbonate.

The foregoing and/or other aspects and utilities embodied in the present disclosure may also be achieved by providing an oral care product including an orally acceptable vehicle and any whitening composition disclosed herein.

In at least one implementation, the oral care product is a mouthwash.

In another implementation, the whitening booster of the oral care product is packaged separately from the orally acceptable vehicle.

The foregoing and/or other aspects and utilities embodied in the present disclosure may also be achieved by providing a method for whitening teeth of a subject, including contacting any whitening composition disclosed herein with a surface of the teeth of the subject in need thereof.

In at least one implementation, the method includes contacting the whitening booster with hydrogen peroxide from the source of hydrogen peroxide prior to contacting the surface of the teeth.

In another implementation, contacting the source of hydrogen peroxide with water to produce the hydrogen peroxide.

In another implementation, contacting the whitening composition with the surface of the teeth at least two times a day.

Further areas of applicability of the present disclosure will become apparent from the detailed description provided hereinafter, it should be understood that the detailed description and specific examples, while indicating some typical aspects of the disclosure, are intended for purposes of illustration only and are not intended to limit the scope of the disclosure.

DETAILED DESCRIPTION

The following description of various aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

The present inventors have surprisingly and unexpectedly discovered that including a whitening booster, such as monopersulfate (MPS), in an oral care product or the whitening composition thereof provided an unexpected and statistically significant increase in whitening efficacy as compared with a conventional hydrogen peroxide oral care product. The inventors have also surprisingly and unexpectedly discovered that the combination of MPS and hydrogen peroxide exhibits synergistic effects (e.g., more than additive) that provide an unexpected and statistically significant enhancement or increase in whitening efficacy for oral care compositions or the whitening composition thereof. Particularly, oral care compositions or the whitening compositions thereof that combine MPS and hydrogen peroxide provide whiter teeth at a faster rate.

Compositions

Compositions disclosed herein may be or include an oral care product or composition and/or a whitening composition thereof. For example, the composition may be an oral care product including a whitening composition, or the whitening composition thereof. In a typical implementation, the compositions may be a mouthwash including a whitening composition, or the whitening composition thereof. The whitening composition may include one or more whitening boosters or enhancer, one or more sources of hydrogen peroxide, one or more buffers, and combinations and mixtures thereof. For example, the whitening composition may include the one or more whitening boosters and the one or more sources of hydrogen peroxide. In another example, the whitening composition may include the one or more whitening boosters, the one or more sources of hydrogen peroxide, and the one or more buffers. As further described herein, the whitening booster may be or include one or more non-peroxide bleaching agents capable of or configured to interact synergistically to enhance the whitening efficacy of the oral care product or the whitening composition thereof.

Any one or more of the whitening boosters, the sources of hydrogen peroxide, and/or the buffers may be maintained separate from one another until the point of use, and at the point of use, the whitening boosters, the sources of hydrogen peroxide, and/or the buffers may be combined, mixed, or otherwise contacted with one another to form the oral care product or the whitening composition thereof. For example, the whitening booster may be maintained separate from the sources of hydrogen peroxide and/or the buffer. In another example, the source of hydrogen peroxide may be maintained separate from the whitening booster and/or the buffer. In yet another example, the buffer may be maintained separate from the whitening booster and/or the source of hydrogen peroxide.

In at least one implementation, any one or more of the whitening boosters, the sources of hydrogen peroxide, and/or the buffers of the whitening composition may be maintained in separate containers until the point of use. For example, any one or more of the whitening boosters, the sources of hydrogen peroxide, and/or the buffers may be maintained in a first vessel or container and the remaining one or more of the whitening boosters, the sources of hydrogen peroxide, and/or the buffers may be maintained in a second vessel or container. Each of the first and second vessels or containers may be stored separate from one another until the point of use. Prior to or at the point of use, the respective contents of the first and second vessels or containers may be mixed, stirred, dispersed, dissolved, combined, or otherwise contacted with one another to generate the whitening composition.

In at least one implementation, any one or more of the whitening boosters, the sources of hydrogen peroxide, and/or the buffers of the whitening composition may be maintained in separate phases until the point of use. For example, the oral care product or the whitening composition thereof may include at least two separate phases that may be combined with one another to generate the whitening composition. For example, any one or more of the whitening boosters, the sources of hydrogen peroxide, and/or the buffers may be maintained in a first phase (e.g., hydrophilic phase) and the remaining one or more of the whitening boosters, the sources of hydrogen peroxide, and/or the buffers may be maintained in a second phase (e.g., hydrophobic phase). In an exemplary implementation, at least the whitening booster and the source of hydrogen peroxide may be maintained in separate phases. In another exemplary embodiment, the source of hydrogen peroxide may be maintained in phase separate from a carrier, such as water. The first or hydrophilic phase may be combined, mixed, or otherwise contacted with the second or hydrophobic phase prior to or at the point of use. A surfactant or surfactant system may aid or facilitate the mixing of the hydrophilic phase with the hydrophobic phase.

The whitening composition or a component thereof may be anhydrous prior to use. For example, the whitening composition or a component thereof may be free or substantially free of water. As used herein, "free" or "substantially free" may refer to a composition that contains less than 5.0 weight %, less than 3.0 weight %, less than 1.0 weight %, less than 0.1 weight %, less than 0.05 weight %, less than 0.01 weight (4), less than 0.005 weight %, or less than 0.0001 weight % based on a total weight of the composition.

In one implementation, contacting the whitening composition or a component thereof with water may initiate the release of hydrogen peroxide. For example, contacting the source of hydrogen peroxide with water may initiate the release of hydrogen peroxide, in another example, the source of hydrogen peroxide may be maintained in the hydrophobic phase, and combining, mixing, or otherwise contacting the hydrophobic phase and hydrophilic phase with one another may initiate the release of hydrogen peroxide from the source of hydrogen peroxide.

Sources of Hydrogen Peroxide

The one or more sources of hydrogen peroxide may be any compound or material capable of or configured to interact or react synergistically with the whitening booster to enhance or increase the whitening efficacy of the oral care product or the whitening composition thereof. For example, the one or more sources of hydrogen peroxide may be or include any compound or material capable of or configured to provide or release hydrogen peroxide that interacts or react synergistically with the whitening booster to enhance or increase the whitening efficacy of the oral care product or the whitening composition thereof. As previously discussed, the sources of hydrogen peroxide may be configured to release hydrogen peroxide when contacted with water. Illustrative sources of hydrogen peroxide may be or include, but are not limited to, hydrogen peroxide, urea peroxide, sodium perborate, calcium peroxide, a cross-linked polyvinylpyrrolidone (PVP) hydrogen peroxide complex, a polyvinylpyrrolidone (PVP) hydrogen peroxide complex, sodium percarbonate, and the like, and combinations thereof. The sources of hydrogen peroxide may also be or include, but are not limited to, PEROXYDONE™ XL 10F complex, which is commercially available from Ashland Inc. of Covington, Ky. In a typical implementation, the source of hydrogen peroxide is hydrogen peroxide.

The amount or concentration of the source of hydrogen peroxide may vary widely, and may depend upon the amount of hydrogen peroxide provided or otherwise delivered by the source of hydrogen peroxide. In at least one implementation, the source of hydrogen peroxide may be present in an amount that provides from greater than 0.0 weight % to less than or equal to 35.0 weight % free hydrogen peroxide, based on a total weight of the oral care product or the whitening composition thereof. For example, the source of hydrogen peroxide may be present in an amount that provides hydrogen peroxide (e.g., free hydrogen peroxide) in an amount of from greater than 0.0 weight about 0.5 weight %, about 1.0 weight %, about 1.5 weight %, about 2.0 weight %, about 2.5 weight %, about 3.0 weight %, about 3.5 weight %, about 4.0 weight %, about 4.5 weight %, about 5.5 weight %, about 6.0 weight %, about 6.5 weight %, about 7.0 weight %, about 7.5 weight %, about 8.0 weight %, about 8.5 weight %, about 9.0 weight %, about 9.5 weight %, or about 10.0 weight % to about 12.0 weight %, about 14.0 weight %, about 16.0 weight %, about 18.0 weight %, about 20.0 weight %, about 22.0 weight %, about 24.0 weight %, about 26.0 weight %, about 28.0 weight %, about 30.0 weight %, about 32.0 weight %, about 34.0 weight %, or less than or equal to about 35.0 weight %, based on a total weight of the oral care product or the whitening composition thereof.

In another implementation, the source of hydrogen peroxide may be present in an amount that provides from greater than 0.0 weight % to less than or equal to 10.0 weight % free hydrogen peroxide, based on a total weight of the oral care product or the whitening composition thereof. For example, the source of hydrogen peroxide may be present in an amount that provides hydrogen peroxide (e.g., free hydrogen peroxide) in an amount of from greater than 0.0 weight %, about 0.5 weight %, about 1.0 weight %, about 1.5 weight %, about 2.0 weight %, about 2.5 weight %, about 3.0 weight %, about 3.5 weight %, about 4.0 weight %, or about 4.5 weight %, to about 5.5 weight about 6.0 weight %, about 6.5 weight %, about 7.0 weight %, about 7.5 weight %, about 8.0 weight %, about 8.5 weight %, about 9.0 weight %, about 9.5 weight %, or about 10.0 weight %, based on a total weight of the oral care product or the whitening composition thereof. In another example, the source of hydrogen peroxide may be present in an amount that provides hydrogen peroxide in an amount of from greater than 0.0 weight % to less than or equal to 10.0 weight %, about 0.5 weight % to about 9.5 weight %, about 1.0 weight % to about 9.0 weight %, about 1.5 weight % to about 8.5 weight %, about 2.0 weight % to about 8.0 weight %, about 2.5 weight % to about 7.5 weight %, about 3.0 weight % to about 7.0 weight %, about 3.5 weight % to about 6.5 weight %, about 4.0 weight % to about 6.0 weight %, or about 4.5 weight % to about 5.5 weight %.

In yet another implementation, the source of hydrogen peroxide may be present in an amount that provides from about 0.1 weight % to less than or equal to 2.0 weight % free hydrogen peroxide, based on a total weight of the oral care product or the whitening composition thereof. For example, the source of hydrogen peroxide may be present in an amount that provides hydrogen peroxide (e.g., free hydrogen peroxide) in an amount of from about 0.1 weight %, about 0.2 weight %, about 0.3 weight %, about 0.4 weight %, about 0.5 weight %, about 0.6 weight %, about 0.7 weight %, about 0.8 weight %, about 0.9 weight %, or about 1.0 weight % to about 1.1 weight %, about 1.2 weight %, about 1.3 weight %, about 1.4 weight %, about 1.5 weight %, about 1.6 weight %, about 1.7 weight %, about 1.8 weight %, about 1.9 weight %, or about 2.0 weight %. In another example, the source of hydrogen peroxide may be present in an amount that provides hydrogen peroxide in an amount of from about 0.1 weight % to about 2.0 weight %, about 0.2 weight % to about 1.9 weight %, about 0.3 weight % to about 1.8 weight %, about 0.4 weight % to about 1.7 weight %, about 0.5 weight % to about 1.6 weight %, about 0.6 weight % to about 1.5 weight %, about 0.7 weight % to about 1.4 weight %, about 0.8 weight % to about 1.3 weight %, about 0.9 weight % to about 1.2 weight %, or about 1.0 weight % to about 1.1 weight %. In yet another example, the source of hydrogen peroxide may be present in an amount that provides hydrogen peroxide in an amount less than or equal to 2.0 weight %, less than or equal to 1.8 weight %, less than or equal to 1.6 weight %, less than or equal to 1.4 weight less than or equal to 1.2 weight %, less than or equal to 1.0 weight %, less than or equal to 0.8 weight %, less than or equal to 0.6 weight %, or less than or equal to 0.4 weight %. In a typical implementation, the source of hydrogen peroxide may be present in an amount that provides hydrogen peroxide in an amount of about 35.0 weight % or less, or about 2.5 weight % or less, or about 2.0 weight % or less, Whitening Booster The whitening booster may be or include any compound or material capable of or configured to interact or react synergistically with the source of hydrogen peroxide or the hydrogen peroxide thereof to enhance the whitening efficacy of the oral care product or the whitening composition thereof. In at least one implementation, the whitening booster may be or include one or more non-peroxide bleaching agents. The whitening booster or the non-peroxide bleaching agent may be water soluble. Illustrative non-peroxide bleaching agents may be or include, but are not limited to, a salt of a peroxymonosulfate or a salt of monopersulfate (MPS). For example, the whitening booster may be or include, but is not limited to, an alkali metal salt of MPS, such as a potassium MPS, sodium MPS, or ammonium MPS. MPS may be provided as a single molecule, a compound, such as a monopersulfate compound or MPS compound, or a complex, such as a monopersulfate complex. For example, the MPS compound may be a mixed salt or triple salt ($2KHSO_5 \cdot KHSO_4 \cdot K_2SO_4$), which is commercially available as OXONE® from DuPont of Wilmington, Del. It should be appreciated that OXONE® has an active oxygen content of about 4.5%. The active oxygen content of the mixed salt is about 5.2% when the salt is purified. The active oxygen content of $KHSO_5$ is about 10.5%. It should further be appreciated that the pure mixed salt has about half as much active oxygen as compared to the pure form, and the 865% pure mixed salt (i.e., OXONE®) has 43% as much active oxygen as compared to the pure form, MPS is also commercially available as CAROAT® from Evonik Corp. of Parsippany, N.J.

In at least one implementation, the whitening booster may be provided as a solid. For example, the whitening booster may be provided as a powder, a tablet, granules, or the like, and the whitening booster may be combined with the remaining components to form the whitening composition. It should be appreciated that the solid may be free or substantially free of water. The solid may be provided in a variety of forms, including, but not limited to, a free flowing granulation, a tablet e.g., effervescing tablet), a caplet, granules, pellets, waters, films, beads, and the like. In another implementation, the whitening booster may be provided as a liquid, mixture, or solution, such as a liquid dispersion of the solid.

The whitening booster may be provided separate from one or more of the remaining components or ingredients of the whitening composition, and at the point of use, the whitening booster may be combined, mixed, dispersed, or otherwise contacted with the one or more remaining components to form the oral care product or the whitening composition thereof. For example, as discussed above, the whitening booster may be provided as a solid and contacted with the one or more remaining components to form or provide the oral care product or the whitening composition thereof.

In at least one implementation, the whitening booster may be provided in an air-tight, moisture-proof container, package, vessel, or the like. Illustrative packages may be or include, but are not limited to, sealed metal foil pouches, blister packs, desiccant capped tubes, and the like. The packages may be made from polymeric materials, such as polyethylene, polypropylene, or the like or copolymers thereof, metallic materials, such as metallic foils (e.g., aluminum), or both the polymeric and metallic materials. The whitening booster may be packaged as a single dose or multiple doses.

The amount or concentration of the whitening booster may vary widely. In at least one implementation, the whitening booster may be provided in an amount greater than 0.0 weight % to about 10 weight %, based on a total weight of the oral care product or the whitening composition thereof. For example, the whitening booster may be provided in an amount from greater than 0.0 weight %, about 0.5 weight %, about 1 weight %, about 1.5 weight %, about 2 weight %, about 2.5 weight %, about 3 weight %, about 3.5 weight %, about 4 weight %, or about 4.5 weight % to about 5 weight %, about 5.5 weight %, about 6 weight %, about 6.5 weight %, about 7 weight %, about 7.5 weight %, about 8 weight %, about 8.5 weight %, about 9 weight %, about 9.5 weight %, or about 10 weight %. In another example, the whitening booster may be provided in an amount from greater than 0.0 weight %, about 0.1 weight %, about 0.2 weight %, about 0.3 weight %, about 0.4 weight %, about 0.5 weight %, about 0.6 weight %, about 0.7 weight %, about 0.8 weight % about 0.9 weight % or about 1.0 weight %, to about 1.1 weight %, about 1.2 weight %, about 1.3 weight %, about 1.4 weight %, about 1.5 weight %, about 1.6 weight %, about 1.7 weight %, about 1.8 weight %, about 1.9 weight %, or about 2.0 weight %. In yet another example, the whitening booster may be provided in an amount from greater than 0.0 weight % to about 2.0 weight %, about 0.1 weight % to about 1.9 weight %, about 0.2 weight % to about 1.8 weight %, about 0.3 weight % to about 1.7 weight %, about 0.4 weight % to about 1.6 weight %, about 0.5 weight % to about 1.5 weight about 0.6 weight % to about 1.4 weight %, about 0.7 weight % to about 1.3 weight %, about 0.8 weight % to about 1.2 weight %, or about 0.9 weight % to about 1.1 weight %.

In at least one implementation, the amount of the whitening booster present in the whitening composition may be at least partially determined by or depend upon the amount of hydrogen peroxide provided or otherwise delivered by the source of hydrogen peroxide. For example, the whitening booster may be provided in an amount such that a ratio of the whitening booster to the amount of hydrogen peroxide provide by the source of hydrogen peroxide may be from about 0.1:1 to about 5:1, or from about 0.1:1 to about 10:1, or from about 0.1:1 to about 15:1. For example, the ratio of the whitening booster to the amount of hydrogen peroxide provide by the source of hydrogen peroxide may be from about 0.01:1, about 0.1:1, about 0.5:1, about 1:1, about 1.5:1, or about 2:11 to about 2.5:1, about 3:1, about 3.5:1, about 4:1, about 4.5:1, about 5:1, about 10:1, or about 15:1. In another example, the ratio of the whitening booster to the amount of hydrogen peroxide provide by the source of hydrogen peroxide may be from about 0.1:1 to about 5:1, about 0.5:1 to about 45:1, about 1:1 to about 4:1, about 1.5:1 to about 3.5:1, or about 2:1 to about 3:1.

Polymers

The oral care product or the whitening composition thereof may include one or more polymers. Illustrative polymers that may be included in the oral care product or the whitening composition thereof may include polyvinylmethyl ether maleic acid copolymers and/or polysaccharides, such as cellulose derivatives, polysaccharide gums, and the like, and combinations thereof. The cellulose derivatives may include carboxymethyl cellulose, and the polysaccharide gums may include xanthum gum or carrageenan gum.

In at least one implementation, the whitening composition may include one or more copolymers, such as a polyvinylmethylether/maleic anhydride (PVM/MA) copolymer, polymaleic anhydride, polystyrene/maleic anhydride (PS/MA) copolymer, polyethylene/maleic anhydride (PE/MA) copolymer, polypropytenelmaleic anhydride (PP/MA) copolymer, polypropylene-graft-maleic anhydride, polyethylene-graft-maleic anhydride, and polyisoprene-graft-maleic anhydride, a phosphate/acrylate copolymer, and the like, and combinations thereof. An illustrative PVM/MA copolymer may include those under the GANTREZ® brand, which is commercially available from ISP of Wayne, N.J.

Fluoride Ion Source

The oral care products and/or the whitening composition thereof may further include one or more fluoride ion sources (e.g., soluble fluoride salts). A wide variety of fluoride ion-yielding materials may be employed as sources of soluble fluoride. Examples of suitable fluoride ion-yielding materials may be found in U.S. Pat. No. 3,535,421 to Briner et al., U.S. Pat. No. 4,885,155 to Parran, Jr. et al., and U.S. Pat. No. 3,678,154 to Widder et al., the disclosures of which are incorporated herein by reference. Illustrative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In a typical implementation, the fluoride ion source includes sodium fluoride. The amount of the fluoride ion source in the oral care composition may be less than 0.08 weight %, less than 0.07 weight %, less than 0.06 weight %, less than 0.05 weight %, or less than 0.04 weight %. For example, the amount of the fluoride ion source may be about 0.05 weight %. In another implementation, the fluoride ion source is present in an amount to provide a total of about 100 to about 20,000 ppm, about 200 to about 5,000 ppm, or about 500 to about 2,500 ppm, fluoride ions.

Surfactants

The oral care product or the whitening composition thereof may include one or more surfactants. For example, the whitening composition may include one or more anionic surfactants, one or more cationic surfactants, one or more zwitterionic surfactants, one or more nonionic surfactants, and mixtures thereof. Examples of suitable surfactants may be found in U.S. Pat. No. 3,959,458 to Agricola et al., U.S. Pat. No. 3,937,807 to Haefele, and U.S. Pat. No. 4,051,234 to Gieske et al., the disclosures of which are incorporated herein by reference in their entirety to the extent they are consistent with the present disclosure.

In at least one implementation, the oral care product or the whitening composition thereof includes at least one anionic surfactant. Illustrative anionic surfactants may include, but are not limited to, water-soluble salts of higher fatty acid monoglyceride monosulfates, such as a sodium salt of a monosulfated monoglyceride of hydrogenated coconut oil fatty acids, such as sodium N-methyl N-cocoyl taurate, sodium cocomonoglyceride sulfate. Illustrative anionic surfactants may also include higher alkyl sulfates. As used herein, "higher alkyl" refers to $C_{6-30}$ alkyl. For example, in a preferred implementation the anionic surfactant is sodium lauryl sulfate. The anionic surfactants may also include higher alkyl-ether sulfates. For example, the anionic surfactants may have a formula $CH_3(CH_2)_mCH_2(OCH_2CH_2)_nOSO_3X$, where m is 6-16, n is 1-6, and X is Na or K. In an exemplary implementation, m is 10, and n is 2, 3, or 4, and X is Na or K. For example, the anionic surfactant may be sodium laureth-2 sulfate $(CH_3(CH_2)_{10}CH_2(OCH_2CH_2)_2OSO_3Na)$. In another implementation, the anionic surfactant may include higher alkyl aryl sulfonates, such as sodium dodecyl benzene sulfonate (sodium lauryl benzene sulfonate), and higher alkyl suifoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. In an exemplary implementation, the anionic surfactant is a water soluble salt of alkyl sulfates having from 10 to 18 carbon atoms in the alkyl radical and water soluble salts of sulfonated monoglycerides of fatty acids having from 10 to 18 carbon atoms. For example, the anionic surfactant may be or include, sodium lauryl sulfate, sodium lauroyl sarcosinate, sodium coconut monoglyceride sulfonates, or the like, and mixtures thereof.

In at least one implementation, the oral care product or the whitening composition thereof may include at least one nonionic surfactant. Accordingly, the oral care product or the whitening composition thereof may include at least one anionic surfactant, at least one nonionic surfactant, or both an anionic surfactant and a nonionic surfactant. The nonionic surfactant may function as an emulsifier. Illustrative nonionic surfactants may include, but are not limited to, poloxamers or the like. For example, the nonionic surfactants may include polysorbate 20, poloxamer 407, poloxamer 338, or the like, and mixtures thereof. The nonionic surfactants may also include, but are not limited to, ethoxylated and hydrogenated ethoxylated castor oils, such as those commonly designated as PEG NN castor oil or PEG NN hydrogenated castor oil, where "NN" designates the number of ethylene oxide units polymerized onto the castor oil to form the nonionic surfactant. For example, the nonionic surfactants may be or include PEG 16, 20, 25, 30, 40, 50, 60, 80, 100, 200, and combinations thereof. In a preferred implementation, the nonionic surfactant is polysorbate 20.

The amount of any one or more of the surfactants in the oral care product or the whitening composition thereof may be from about 0.010 weight %, about 0.020 weight %, about 0.030 weight %, about 0.040 weight %, about 0.045 weight %, about 0.049 weight %, or about 0.050 weight % to about 0.051 weight %, about 0.055 weight %, about 0.060 weight %, about 0.065 weight %, about 0.070 weight %, about 0.075 weight about 0.080 weight %, or greater. In another example, the amount of any one or more of the surfactants in the oral care product or the whitening composition thereof may be about 0.010 weight % to about 0.090 weight %, about 0.020 weight % to about 0.080 weight %, about 0.030 weight % to about 0.070 weight %, about 0.040 weight % to about 0.060 weight %, about 0045 weight % to about 0.055 weight %, or about 0.050 weight % to about 0.051 weight %. In yet another example, the amount of any one or more of the surfactants in the oral care product or the whitening composition thereof may be greater than 0.010 weight greater than 0.020 weight %, greater than 0.030 weight %, greater than 0.040 weight %, greater than 0.045 weight %, greater than 0.049 weight %, or greater than 0.050 weight %. The amount of any one or more of the surfactants in the oral care product or the whitening composition thereof may also be from about 0.10 weight %, about 0.20 weight %, about 0.30 weight %, about 0.40 weight %, about 0.45 weight %, about 0.49 weight %, or about 0.50 weight % to about 0.51 weight %, about 0.55 weight %, about 0.60 weight %, about 0.65 weight %, about 0.70 weight %, about 0.75 weight %, about 0.80 weight or greater. In another example, the amount of any one or more of the surfactants in the oral care product or the whitening composition thereof may be about 0.10 weight % to about 0.90 weight %, about 0.20 weight % to about 0.80 weight %, about 0.30 weight % to about 0.70 weight %, about 0.40 weight % to about 0.60 weight %, about 0.45 weight % to about 0.55 weight %, or about 0.50 weight % to about 0.51 weight %. In yet another example, the amount of any one or more of the surfactants in the oral care product or the whitening composition thereof may be greater than 0.10 weight %, greater than 0.20 weight %, greater than 0.30 weight %, greater than 0.40 weight 0.10 greater than 0.45 weight %, greater than 0.49 weight %, or greater than 0.50 weight %.

Flavoring Agents

The oral care product or the whitening composition thereof may also include one or more flavoring agents. Illustrative flavoring agents may include, but are not limited to, essential oils and various flavoring aldehydes, esters, alcohols, and the like. The flavoring agents may also include, but are not limited to, sweeteners, sucralose, dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof (e.g., sodium saccharin), dipeptide-based intense sweeteners, cyclamates, dihydrochalcones and mixtures thereof. Examples of the essential oils include oils of spearmint, peppermint, wintergreen, sassafras, clove, sage, eucalyptus, marjoram, cinnamon, lemon, lime, grapefruit, and orange. In another example, the flavoring agents may include menthol, carvone, and anethole. In a preferred implementation, the flavoring agent includes peppermint and spearmint. In a more preferred implementation, the flavoring agent includes a Firmenich Newman Flavor.

The amount of the flavoring agent in the oral care product or the whitening composition thereof may be less than 1.0 weight %, less than 0.9 weight %, less than 0.8 weight %, or less than 0.7 weight %. For example, the amount of the flavoring agent in the oral care product or the whitening composition thereof may be about 0.0 weight % to about 1.0 weight %, about 0.5 weight % to about 0.9 weight %, about 0.7 weight % to about 0.8 weight %. In a preferred implementation, the amount of the flavoring agent in the oral care product or the whitening composition thereof is about 0.01 weight % to about 0.4 weight %, preferably about 0.1 weight % to about 0.3 weight %, or about 0.2 weight %.

Humectants

The oral care product or the whitening composition thereof may include one or more humectants. The humectants may be capable of or configured to reduce evaporation and lower water activity. It should be appreciated that the humectants may also be capable of imparting desirable sweetness or flavor to the oral care product or the whitening composition thereof. Illustrative humectants may include, but are not limited to polyhydric alcohols, such as glycerin, sorbitol, xylitol, propylene glycol, as well as other polyols, and mixtures thereof. In at least one implementation, the one or more humectants are present in an amount of from about 10 weight % to about 20 weight % based on a total weight of the oral care product of the whitening composition thereof.

Water

The oral care product or the whitening composition thereof may include water. Water of the oral care product or the whitening composition thereof may be deionized and free of organic impurities. Water may make up the balance of the oral care product or the whitening composition thereof. For example, the amount of water in the oral care product or the whitening composition thereof may be from about 10 weight % to 90 weight %, about 40 weight % to about 85 weight %, or about 60 weight % to about 80 weight %. In another example, the amount of water in the oral care product or the whitening composition thereof may be at least 60 weight %, at least 65 weight %, at least 70 weight %, at least 78 weight %, or at least 79 weight %. The amount of water in the oral care product or the whitening composition thereof may include free water added and water introduced with other components or materials of the oral care product or the whitening composition thereof. For example, the amount of the water in the oral care product or the whitening composition thereof may include free water and water associated with the humectants, flavoring agents, or any other component of the oral care product or the whitening composition thereof.

pH Modifying Agents/Buffers

The oral care product or the whitening composition thereof may optionally include one or more pH modifying agents. For example, the oral care product or the whitening composition thereof may include one or more acidifying agents and/or one or more basifying agents to reduce and/or increase the pH, respectively. The oral care product or the whitening composition thereof may also include one or more buffeting agents to control or modulate the pH within a predetermined or desired range. Illustrative buffering agents may include, but are not limited to, anhydrous carbonates, sesquicarbonates, sodium bicarbonate, sodium phosphate, sodium hydroxide, sodium carbonate, sodium acid pyrophosphate, citric acid, sodium citrate, phosphoric acid, sorbitol, polysorbate, and the like, and mixtures and combinations thereof. Sodium phosphate may include, monosodium phosphate ($NaH_2PO_4$), disodium phosphate ($Na_2HPO_4$), trisodium phosphate ($Na_3PO_4$), and mixtures thereof. In a preferred implementation, the buffering agent is anhydrous sodium phosphate dibasic or disodium phosphate.

In at least one implementation, the acidifying, basifying, and/or buffering agents may be included in the oral care product or the whitening composition thereof to provide the oral care composition with a pH between 2 to 10, 2 to 8, 3 to 9, 4 to 8, 6 to 10, or 7 to 9. Additional orally acceptable pH modifying agents may be used, such as carboxylic, phosphoric, and sulfonic acids, acid salts (e.g., monosodium citrate, disodium citrate, monosodium malate, etc.), alkali metal hydroxides, such as sodium hydroxide, carbonates, such as sodium carbonate, bicarbonates, sesquicarbonates, borates, silicates, phosphates (e.g., monosodium phosphate, tri sodium phosphate, pyrophosphate salts, etc.), imidazole and mixtures thereof. The one or more pH modifying agents may be present in an amount effective to maintain the oral care product or the whitening composition thereof in an orally acceptable pH range. In a preferred implementation, the pH modifying agents includes any one or more of sodium bicarbonate, citric acid, phosphoric acid, sorbitol, polysorbate, and combinations and mixtures thereof.

Additional Ingredients

It should be appreciated to one having ordinary skill in the art, that the oral care products and/or the whitening composition thereof may include other additional ingredients/components. For example, the oral care products and/or the whitening composition thereof may include anti-caries agents, desensitizing agents, viscosity modifiers, diluents, mouth feel agents, colorants, preservatives, and the like, and combinations and mixtures thereof. It should further be appreciated by one having ordinary skill in the art that while general attributes of each of the above categories of materials may differ, there may be some common attributes and any given material may serve multiple purposes within two or more of such categories of materials.

In at least one implementation, the additional ingredients/components may include one or more active materials configured to prevent and/or treat one or more conditions and/or disorders of the oral cavity. For example, the one or more active materials may be configured to prevent and/or treat one or more conditions and/or disorders of hard and/or soft tissue of the oral cavity. The active materials may also be configured to prevent and/or treat one or more physiological disorders and/or conditions, and/or provide a cosmetic benefit to the oral cavity.

In at least one implementation, the oral care products and/or the whitening composition thereof may include an anticalculus agent. Generally, anticalculus agents may not be compatible with some whitening compositions, however, implementations of the present disclosure may incorporate anticalculus agents and the whitening composition into a single phase oral care product. Illustrative anticalculus agents may include, but are not limited to, phosphates and polyphosphates (e.g., pyrophosphates), polyaminopropanesulfonic acid (AMPS), hexametaphosphate salts, zinc citrate trihydrate, polypeptides, polyolefin sulfonates, polyolefin phosphates, diphosphonates. In a typical implementation, the anticalculus agents includes tetrasodium pyrophosphate (TSPP), sodium tripolyphosphate (STPP), or a combination thereof.

The oral care products and/or the whitening composition thereof may optionally include one or more antimicrobial agents and/or one or more preservatives such as, methylisothiazolinone (MIT), sodium benzoate, potassium sorbate, benzyl alcohol, and combinations thereof. In another example, the oral care composition may include one or more antibacterial agents selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, other metal ions e.g., stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol, and other piperidine derivatives, nicin preparations, chlorite salts; and mixtures of any of the foregoing. In a typical implementation, the antibacterial agent includes cetylpyridinium chloride (CPC). For example, all of the dual-phase mouthwash compositions disclosed herein may include CPC as an antibacterial agent.

The oral care products and/or the whitening composition thereof may include an antioxidant. Any orally acceptable antioxidant may be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and the like, and combinations and mixtures thereof.

Vehicle

The whitening composition may form at least a portion of or be used in one or more oral care products. Illustrative oral care products may include, but are not limited to, a mouthwash, a toothpaste (dentifrice), a prophylactic paste, a tooth powder, a tooth polish, a tooth gel (e.g., a whitening gel), a chewing gum, a lozenge, a whitening strip, a paint-on gel, varnish, veneer, and tube, syringe or dental tray comprising a gel or paste, or a gel or paste coated on an application support such as dental floss or a toothbrush (e.g., a manual, electric, sound, a combination thereof or ultrasound toothbrush). In a typical implementation, the whitening composition may form at least a portion of or be used with a mouthwash. For example, the whitening composition may typically be a mouthwash, such as a dual-phase mouthwash or a single-phase mouthwash. In another example, the whitening composition or a component thereof may be a solid (e.g., powder) to be combined with the mouthwash. The whitening composition may be mixed, dispersed, dissolved, combined, or otherwise contacted with an orally acceptable vehicle to form the oral care product (e.g., the mouthwash). In an exemplary implementation, the orally acceptable vehicle may include glycerin and/or water. In at least one implementation, the orally acceptable vehicle may include one or more humectants.

All ingredients for use in the compositions described herein should be orally acceptable. By "orally acceptable" as the term is used herein is meant an ingredient that is present in a composition as described in an amount and form that does not render the composition unsafe for use in the oral cavity.

Method

The present disclosure may provide methods for whitening teeth in a human or animal subject with an oral care product and/or the whitening composition thereof. For example, the disclosure may provide methods for whitening surfaces and/or dentin of the teeth in a human or animal subject with an oral care product and/or the whitening composition thereof. As used herein "animal subject" may include higher order non-human mammals such as canines, felines, and horses.

The method may include storing and/or containing the whitening composition or a component thereof in a stable form until the time or point of use. For example, the method may include storing and/or containing the whitening booster (e.g., MPS) and/or the source of hydrogen peroxide in a stable form until the time of use. The method may also include admixing, stirring, combining, mixing, or otherwise contacting the components of the whitening composition with one another to form the whitening composition, and contacting the whitening composition with the surfaces of the teeth. In at least one implementation, contacting the components of the whitening composition with one another to form the whitening composition may include admixing, stirring, combining, mixing, or otherwise contacting a first phase (e.g., hydrophilic phase) with a second phase (e.g., hydrophobic phase). The method may also include combining, mixing, or otherwise contacting the source of hydrogen peroxide with water to generate hydrogen peroxide, and contacting the hydrogen peroxide with the whitening booster.

The method may also include swishing the oral care product, brushing the teeth with the oral care product, or disposing the oral care product in a dental tray and disposing the dental tray in the oral cavity such that the contents thereof contact the surfaces of the teeth. In some implementations, the oral care product (e.g., the mouthwash) or the whitening composition thereof may be applied directly to the teeth using a delivery device, such as a pen, (e.g., a COLGATE® whitening pen or a COLGATE® ACTIS™ whitening pen, Colgate-Palmolive Company, New York, N.Y.), a liquid stick having an applicator, such as a felt tip, brush, roller ball, or non-woven pad, sufficient to effect whitening.

The oral care product and/or the whitening composition thereof may be applied and/or contacted with the surfaces of the teeth at predetermined intervals. For example, the oral care product and/or the whitening composition thereof may be applied and/or contacted with the surfaces of the teeth on a daily basis, at least one time a day for multiple days, at least two times a day for multiple days, or alternatively every other day. The oral care product and/or the whitening composition thereof may be utilized for up to 1 day, up to 2 days, up to 7 days, up to 10 days, up to 2 weeks, up to 3 weeks, up to 4 weeks, up to 6 weeks, up to 8 weeks, or greater.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The whitening efficacy of varying amounts of a whitening booster, namely monopersulfate (MPS), was evaluated and compared to 1% hydrogen peroxide. Particularly, artificially stained bovine teeth having L* values from about 57 to about 65 were obtained from Therametric Technologies, Inc., and exposed to varying amounts of MPS and 1% hydrogen peroxide. A hydrogen peroxide (HP) solution (1% solution) and three MPS solutions (0.5% solution, 1% solution, and 2% solution) were prepared by dissolving appropriate amounts of MPS (CAROAT® 47% MPS) and HP, respectively, in a phosphate buffer (pH 7.5-8). Each of the bovine teeth were soaked in 20 mL of a respective MPS or HP solution for two minutes (min). After two min, the MPS or HP solutions were removed and the stained teeth were rinsed three times with deionized water. A single treatment included a single soaking for two min followed by rinsing.

The L*, a*, b* values were measured with a hand-held spectrophotometer after every two treatments, and the measurements were recorded through 14 treatments. The L*, a*, b* values were compared to the baseline values to calculate the change in the whiteness of each of the teeth. It should be appreciated that the whiteness index (W*) is a measure of overall color change relative to pure white, and is given by formula (1), and the change in whiteness index (ΔW*) is measured by formula (2). The change in whiteness index (ΔW*), or whitening efficacy, is summarized in Table 1.

$$W^* = ((L^* - 100)^2 + (a^*)^2 + (b^*)^2)^{1/2} \quad (1)$$

$$\Delta W^* = W^*_{treated} - W^*_{baseline} \quad (2)$$

TABLE 1

Whitening Efficacy (ΔW*) of MPS vs. HP

| | | Number of Treatmtents | | | | | | | |
|---|---|---|---|---|---|---|---|---|---|
| | | 0 | 2 | 4 | 6 | 8 | 10 | 12 | 14 |
| 0.5% MPS | ΔW* | 0.00 | 4.13 | 6.06 | 7.90 | 8.49 | 8.74 | 9.08 | 9.04 |
| 1% MPS | ΔW* | 0.00 | 3.76 | 4.41 | 5.78 | 6.53 | 7.04 | 8.15 | 8.27 |
| 2% MPS | ΔW* | 0.00 | 4.59 | 6.26 | 8.07 | 8.67 | 8.85 | 9.14 | 9.26 |
| 0.1% HP | ΔW* | 0.00 | 0.15 | 0.22 | 0.38 | 0.6 | 0.69 | 0.73 | 1.01 |

It should be appreciated that the active oxygen content of 1% HP is equivalent to about 0.5% MPS. As demonstrated in Table 1, however, 0.5% MPS surprisingly and unexpectedly provided a statistically significant increase in whitening efficacy on the stained teeth than the 1% HP solution.

Example 2

The whitening efficacy of MPS in a non-whitening mouthwash (MW) was compared with a whitening MW. An MPS composition was prepared by combining the ingredients/components according to Table 2. The non-whitening MW and the whitening MW were prepared by combining the ingredients/components according to Table 3 and 4, respectively.

TABLE 2

MPS Composition

| Ingredient | (Weight %) |
|---|---|
| Sodium Bicarbonate | 47.0 |
| MPS | 23.0 |
| Sodium Carbonate | 30.0 |

TABLE 3

Composition of Non-Whitening Mouthwash

| Ingredient | (Weight %) |
|---|---|
| Water | 79.2674 |
| Surfactants | 0.4 |
| Humectants | 20.0 |
| Buffers | 0.0720 |
| Flavor and Color | 0.1656 |
| Antibacterial | 0.075 |
| Sweetener | 0.02 |
| Total | 100.000 |

TABLE 4

Composition of 2% Hydrogen Peroxide Whitening Mouthwash

| Ingredient | (Weight %) |
|---|---|
| Water | 69.61 |
| Polymer | 0.80 |
| Sweetener | 0.05 |
| Buffers | 6.95 |
| Humectants | 14.5 |
| 35% hydrogen Peroxide | 5.71 |
| Surfactant | 2.17 |
| Flavor | 0.20 |
| Total | 100.000 |

To evaluate the whitening efficacy (ΔW*) of the MPS in the non-whitening MW and the whitening MW, stained bovine teeth having L* values from about 57 to about 65 were submerged in deionized water. 1 gram (g) of the MPS composition was combined or dissolved in 10 mL of the non-whitening MW and stirred to provide a 1% MPS mouthwash (MW). Similar to Example 1, the stained teeth were separated from the deionized water and soaked in the 1% MPS MW and the 2% HP MW for 1 min. After soaking, the teeth were removed from their respective solutions and allowed to sit for an additional minute before rinsing three times with deionized water. After every two treatments, the L*, a*, b* values were measured. The whitening efficacy (ΔW*) is summarized in Table 5.

TABLE 5

Whitening Efficacy (ΔW*) of MPS in Non-whitening MW vs. 2% HP MW

| | | Number of Treatments | | | | | | | |
|---|---|---|---|---|---|---|---|---|---|
| | | 0 | 2 | 4 | 6 | 8 | 10 | 12 | 14 |
| 2% HP MW | ΔW* | 0.00 | 1.1 | 1.5 | 1.9 | 1.9 | 2.1 | 2.3 | 2.3 |
| 1% MPS + Non-whitening MW | ΔW* | 0.00 | 2.2 | 3.1 | 4.0 | 4.7 | 5.5 | 6.2 | 6.8 |

As demonstrated in Table 5, the whitening efficacy of the 1% MPS MW, including the MPS composition in combination with a commercially available non-whitening MW was significantly better than the whitening efficacy of a commercially available 2% HP MW.

Example 3

The whitening efficacy ($\Delta W^*$) of MPS in a whitening MW was compared with the whitening MW alone. 1 g of the MPS composition (Table 2 of Example 2) was combined with 10 mL of the 2% HP MW of (Table 4 of Example 2) to prepare the 1% MPS in 2% HP MW solution. The procedure was the same as that of Example 2 for evaluating the whitening efficacy. The results of the whitening efficacy are summarized in Table 6.

TABLE 6

Whitening Efficacy ($\Delta W^*$) of MPS in 2% HP MW vs. 2% HP MW

| | | Number of Treatments | | | | | | |
|---|---|---|---|---|---|---|---|---|
| | | 0 | 2 | 4 | 6 | 8 | 10 | 12 | 14 |
| 2% HP MW | $\Delta W^*$ | 0.00 | 1.1 | 1.7 | 2.4 | 2.5 | 2.9 | 3.2 | 3.5 |
| 1% MPS + 2% HP MW | $\Delta W^*$ | 0.00 | 3.8 | 5.8 | 6.7 | 7.4 | 8.1 | 8.7 | 8.8 | sition was combined with 15 g of water or the 2% HP MW (Table 4, Example 2). The 2% HP MW was used as is. Stained bovine teeth were separated from the deionized water from which they were soaking, and each of the stained bovine teeth were then soaked in the respective solution (1) 2% HP MW, (2) MPS+water, and (3) MPS+2% HP MW. Each of the teeth were soaked in the respective solution for 1 min, and then rinsed with running tap water for 20 secs. After every two treatments, the $L^*$, $a^*$, $b^*$ values were measured. The whitening efficacy ($\Delta W^*$) is summarized in Table 8. It should be appreciated that the "expected" whitening efficacy of MPS in combination with the 2% HP MW was calculated by summing the actual whitening efficacy of the 2% HP MW and the actual whitening efficacy of the MPS+water.

TABLE 7

MPS Composition

| Ingredient | (Weight %) |
|---|---|
| Sodium Bicarbonate | 77.0 |
| MPS | 23.0 |

TABLE 8

Whitening Efficacy ($\Delta W^*$) of MPS + 2% HP MW vs. 2% HP MW vs. MPS + Water

| | | Number of Treatments | | | | | | | |
|---|---|---|---|---|---|---|---|---|---|
| | | 0 | 2 | 4 | 6 | 8 | 10 | 12 | 14 | 20 |
| 2% HP MW | $\Delta W^*$ | 0.00 | 0.642 | 1.097 | 1.467 | 1.966 | 1.637 | 1.859 | 1.995 | 2.748 |
| | Std. Dev. | 0.00 | 0.373 | 0.386 | 0.418 | 0.182 | 0.536 | 0.485 | 0.658 | 0.455 |
| MPS + Water | $\Delta W^*$ | 0.00 | 1.948 | 3.038 | 3.784 | 4.487 | 4.947 | 5.484 | 5.893 | 6.858 |
| | Std. Dev. | 0.00 | 0.062 | 0.120 | 0.243 | 0.688 | 0.512 | 0.509 | 0.582 | 0.846 |
| MPS + 2% HP MW (Expected) | $\Delta W^*$ | 0.00 | 2.590 | 4.135 | 5.251 | 6.453 | 6.584 | 7.343 | 7.888 | 9.606 |
| MPS + 2% HP MW (Actual) | $\Delta W^*$ | 0.00 | 2.651 | 5.343 | 6.728 | 7.884 | 8.890 | 9.932 | 10.541 | 11.911 |
| | Std. Dev. | 0.00 | 1.052 | 1.704 | 1.799 | 1.726 | 1.926 | 1.791 | 1.780 | 1.429 |

As demonstrated in Table 6, the whitening efficacy of the 1% MPS in combination with the 2% HP MW was significantly greater than the 2% HP MW alone.

Example 4

The synergistic increase in whitening efficacy from the interaction of MPS and HP was evaluated. Particularly, the whitening efficacy ($\Delta W^*$) of MPS in combination with the 2% HP MW was compared with the MPS alone and the 2% HP MW alone. As further detailed below, the synergistic relationship was more than additive and was nothing short of surprisingly and unexpected.

To evaluate the synergy between MPS and HP, an MPS composition was prepared by combining the ingredients/components according to Table 7. 1.4 g of the MPS compo- As demonstrated in Table 8, the combination of the MPS with the 2% HP MW provided synergistic results that were nothing short of surprising and unexpected. Particularly, the actual whitening efficacy of the combination of MPS and the 2% HP MW was significantly greater than the expected whitening efficacy; and thus, more than additive. It should be appreciated that the increase in the whitening efficacy between the expected and actual was statistically significant. The synergistic effect is shown in as little as two treatments, but increases substantially with additional treatments. Accordingly, it was surprisingly and unexpectedly discovered that the combination of MPS and hydrogen peroxide exhibits synergistic effects that provided a statistically significant enhancement or increase in the whitening efficacy for oral care compositions or the whitening composition thereof. Particularly, oral care compositions or the whitening compositions thereof that combine MPS and hydrogen peroxide provide whiter teeth at a faster rate.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A whitening composition, comprising a whitening booster and a source of hydrogen peroxide, wherein the whitening booster comprises potassium monopersulfate in an amount from 0.5 to 10 weight %, and wherein the source of hydrogen peroxide is hydrogen peroxide in an amount to provide from 0.5 to 20 weight % of free hydrogen peroxide, and wherein the whitening composition is a mouthwash.

2. The whitening composition of claim 1, wherein the whitening composition comprises the potassium monopersulfate in an amount from 0.5 to 5 weight %.

3. The whitening composition of claim 1, wherein the whitening composition comprises the potassium monopersulfate in an amount from 0.5 to 1.5 weight %.

4. The whitening composition of claim 1, wherein the whitening composition comprises the hydrogen peroxide in an amount to provide from 0.5 to 6.0% of free hydrogen peroxide.

5. The whitening composition of claim 1, further comprising an orally acceptable vehicle, wherein the whitening booster is maintained separate from the orally acceptable vehicle and the source of hydrogen peroxide until the point of use.

6. The whitening composition of claim 1, wherein the whitening composition comprises the hydrogen peroxide in an amount to provide from 0.5 to 3.0% of free hydrogen peroxide.

7. The whitening composition of claim 1, further comprising a buffering agent.

8. The whitening composition of claim 7, wherein the buffering agent comprises at least one of sodium bicarbonate and sodium carbonate.

9. The whitening composition of claim 1, wherein the whitening composition comprises the potassium monopersulfate in an amount from 0.5 to 5 weight % and the hydrogen peroxide in an amount to provide from 0.5 to 6.0% of free hydrogen peroxide.

10. The whitening composition of claim 1, wherein the whitening composition comprises the potassium monopersulfate in an amount from 0.5 to 1.5 weight % and the hydrogen peroxide in an amount to provide from 0.5 to 3.0% of free hydrogen peroxide.

11. The whitening composition of claim 1, wherein the whitening composition comprises from 10 to 90 weight % water.

12. A method for whitening teeth of a subject, comprising contacting the whitening composition according to claim 1 with a surface of the teeth of the subject in need thereof.

13. The method of claim 12, wherein the whitening composition is formed by combining a composition comprising the whitening booster with a composition comprising the source of hydrogen peroxide at the time of use.

14. The method of claim 13, wherein the composition comprising the whitening booster is a hydrophilic phase, and the composition comprising the source of hydrogen peroxide is a hydrophobic phase.

15. The method of claim 12, further comprising contacting the whitening composition with the surface of the teeth at least two times per day.

16. The whitening composition of claim 1, wherein the composition further comprises at least one humectant selected from glycerin, sorbitol, xylitol, propylene glycol, and other polyols, and at least one surfactant selected from anionic surfactants, cationic surfactants, zwitterionic surfactants, and nonionic surfactants.

* * * * *

UNITED STATES PATENT AND TRADEMARK OFFICE
CERTIFICATE OF CORRECTION

PATENT NO. : 10,744,075 B2
APPLICATION NO. : 16/011739
DATED : August 18, 2020
INVENTOR(S) : Cajetan Dogo-Isonogie et al.

It is certified that error appears in the above-identified patent and that said Letters Patent is hereby corrected as shown below:

In Column 4, Line 54, "(4)" should be changed to – % –.

In Column 4, Line 60, "peroxide, in" should be changed to – peroxide. In –.

In Column 7, Line 8, "865%" should be changed to – 86.5% –.

In Column 7, Line 20, "e.g.," should be changed to – (e.g., –.

In Column 7, Line 21, "waters" should be changed to – wafers –.

In Column 7, Line 63, "0.8 weight" should be changed to – "0.8 weight %" –.

In Column 7, Line 64, "0.9 weight" should be changed to – "0.9 weight %" –.

In Column 8, Line 24, "2:11" should be changed to – 2:1 –.

In Column 8, Line 29, "45:1" should be changed to – 4.5:1 –.

In Column 8, Line 46, "polypropytenelmaleic" should be changed to – polypropylene/maleic –.

In Column 9, Line 43, "suifoacetates" should be changed to – sulfoacetates –.

In Column 10, Line 15, "0.075 weight" should be changed to – "0.075 weight %" –.

In Column 10, Line 21, "0045" should be changed to – 0.045 –.

In Column 10, Line 36, "0.80 weight" should be changed to – "0.80 weight %" –.

In Column 10, Line 47, "0.10" should be changed to – % –.

Signed and Sealed this
Third Day of November, 2020

Andrei Iancu
*Director of the United States Patent and Trademark Office*

CERTIFICATE OF CORRECTION (continued)
U.S. Pat. No. 10,744,075 B2

In Column 11, Line 64, "buffeting" should be changed to – buffering –.

In Column 12, Line 20, "tri sodium" should be changed to – trisodium –.

In Column 13, Line 26, "piperidine" should be changed to – piperdino –.